United States Patent [19]

Janata et al.

[11] 4,322,680

[45] Mar. 30, 1982

[54] CHEMICALLY SENSITIVE JFET TRANSDUCER DEVICES UTILIZING A BLOCKING INTERFACE

[75] Inventors: Jiri Janata; Roland W. Ure, Jr., both of Salt Lake City, Utah

[73] Assignee: University of Utah Research Foundation, Salt Lake City, Utah

[21] Appl. No.: 126,746

[22] Filed: Mar. 3, 1980

[51] Int. Cl.³ ............................................. G01N 27/00
[52] U.S. Cl. ............................... 324/71 SN; 324/71 R
[58] Field of Search .......................... 324/71 R, 71 SN

[56] References Cited

U.S. PATENT DOCUMENTS 3,356,864 12/1967 Giaever ........................... 324/71 SN
3,469,184 9/1969 Lambe et al. .................... 324/71 SN
4,158,807 6/1979 Senturia ........................... 324/71 SN

OTHER PUBLICATIONS

Moss et al., "Hydrogen, Calcium and Potassium Ion-Sensitive FET Transducers", IEEE Trans. on Biomedical Engineering, vol. BME-25, No. 1, (Jan. 1978) pp. 49-54.

Primary Examiner—Michael J. Tokar
Attorney, Agent, or Firm—Thorpe, North, Western & Gold

[57] ABSTRACT

A chemically sensitive junction field effect transistor transducer capable of selectively detecting and measuring chemical properties of substances to which the transducer is exposed. The transducer includes a substrate material, a semiconductor layer having a doping polarity laid over the surface of the substrate, a "source" contact connected to one part of the semiconductor layer, a "drain" contact connected to another part, and a chemically sensitive blocking interface gate structure overlying the upper surface of that portion of the semiconductor layer between the source and drain contacts. The gate structure is adapted to interact with selected chemical substances in the substance being tested and to produce an electric field in relation to the presence, concentration, or activity thereof. This electric field, in turn, causes a modulation of the depletion region in the semiconductor layer that affects the conductivity thereof, and hence the amount of source-drain current that can flow through the transducer. The gate structure also serves as a blocking interface and prevents current from flowing through the gate structure. The chemically sensitive blocking interface gate structure may include numerous configurations and materials adapted for sensing various chemical or biochemical properties.

37 Claims, 13 Drawing Figures

CHEMICALLY SENSITIVE JFET TRANSDUCER DEVICES UTILIZING A BLOCKING INTERFACE

BACKGROUND OF THE INVENTION

1. Field of the Invention

This invention relates to chemically sensitive transducers, and more particularly to a junction field effect transistor (JFET) type of chemically sensitive transducer adapted for detection and measurement of various chemical properties such as ion activity.

2. Prior Art

Field effect transistors (FETs) have recently been proposed for use as the basic or implementing device in chemically sensitive transducers. See, e.g., U.S. Pat. No. 4,020,830 and references cited therein. See also Zemel, *Ion-Sensitive Field Effect Transistors And Related Devices*, 47 Analytical Chemistry, No. 2, 255 A-68A (1975). The FETs employed in these devices have typically been metal oxide semi-conductor FETs (MOSFET), sometimes refered to as insulated gate FETs, or IG-FETs. Because these devices are sensitive to chemical properties of solutions to which they are exposed, they are referred to generally as CHEMFETs.

Prior art CHEMFET transducers (MOSFETs or IGFETs) have relied on a chemically sensitive membrane deposited over the insulated gate. The function of this chemically sensitive membrane is to interact with the solution under test, and to create an electric potential that is proportional to this interaction. This electric potential is in turn sensed at the semiconductor surface of the device, thereby inducing a channel through which current can flow from the source of the FET device to the drain (or vice versa). The electron concentration in the channel that is thus induced, and hence the amount of current that can flow, is a function of the strength of the electric potential, which in turn is a function of the chemical activity occurring at the solution-membrane interface. Current flow between the source and drain of the FET is *enhanced* by the presence of an electric field at the gate. By selectively choosing the type of membrane that is placed over the insulated gate, unique chemical properties of solutions can be detected by these prior art devices. For example, the presence, concentration, or activity of a particular ion, enzyme, antigen, etc., can be detected by selectively using a particular membrane that would absorb or interact with that particular item. Moreover, use of several different chemically sensitive membranes, each over a different IGFET on the same substrate, thus results in a multi-transducer CHEMFET which could simultaneously sense several selected chemical properties of the solution.

SUMMARY OF THE INVENTION

It is an object of the present invention to provide an improved field-effect transistor (FET) transducer for detecting and measuring chemical properties of substances to which the transducer is exposed.

It is another object of the present invention to provide a compact, accurate, stable, and yet inexpensive, selective chemical sensitive FET transducer that does not require the use of insulating layers or chemically sensitive membranes.

It is also an object of the present invention to provide such a transducer that has a long life and which can be used in a variety of chemical measuring applications.

It is a further object of the present invention to provide a chemically sensitive transducer, in accordance with one aspect of the invention, whose chemical sensitivity may be selected by altering the gate structure of the FET devices employed within the invention, including the optional use of chemical sensitive membranes.

It is still a further object of the present invention to provide, in accordance with another aspect of the invention, a simple, easily manufactured, inexpensive structure which includes a plurality of such transducers.

Still a further object of the present invention is to provide such a transducer whose design and geometry make it suitable for both in vivo in in vitro measuring applications.

The above and other objects of the present invention are realized in illustrative embodiments of a selective chemical sensitive FET transducer, or CHEMFET, that requires neither: (1) the use of an insulating layer between the sensitive gate region of the FET device and the substance under test, nor (2) the use of a chemically sensitive membrane.

Rather than using a layer of insulating material to keep current from flowing between the semiconductor and the substance under test, the invention disclosed herein employs a blocking interface for that purpose. The blocking interface used by the invention may be one of three types: (1) a metal-semiconductor (Schottky) interface; (2) a solution-semiconductor (blocking electrode) interface; or (3) a P-N junction interface. Although all three types of these blocking interfaces are known in the prior art of semiconductor technology, none have been employed in the combination and manner disclosed herein.

The blocking interface transducer that is the subject of this invention also does not require use of a chemically sensitive membrane, although such a membrane can be used, if desired, to improve the selectivity of the device. The elimination of this membrane greatly facilitates the fabrication of the transducer. Chemical sensitivity is maintained without the membrane by selectively choosing the materials from which the blocking interface is made. Typical materials that can be used to achieve this selective chemical sensitive function are disclosed in the detailed description of the preferred embodiment which follows.

A principle distinction between the present invention and the prior art devices, other than elimination of the above mentioned insulating material and chemically sensitive membrane, is the mode of operation by which the present invention operates. The CHEMFET sensor herein disclosed operates on a principle similar to that of a junction field effect transistor (JFET) device or a Schottky barrier FET, meaning that a channel through which current may flow from the source to the drain is inherent in the device. Thus, current flows through the device without any gate structure at all. When a gate structure is placed on the device (i.e., when some sort of material is placed over the gate region—that region over the channel between the source and drain through which the current flows), a depletion region is formed in the channel which partially or entirely reduces electrical conduction in the channel. The gate structure is made of a material adapted to react or interact with the chemical properties of the solution under test. This interaction creates an electric field that changes the thickness of the depletion region and thus changes (makes narrower or wider) the channel that already exists between the source and the drain. That is, current flow is depleted by the presence of an electric field at the gate. Because of the blocking characteristics of the gate structure interface, no significant current flows from the solution through the junction or interface. Thus, as mentioned previously, there is no need for an insulating gate material.

The amount of current flowing between the source and drain in a JFET type of CHEMFET is a function of the strength of the electric field generated at the gate structure. In turn, the strength of this electric field is a function of both the gate structure itself, that is the materials which comprise it, and the chemical properties of the solution under test. Thus, a measure of the current flowing between the source and drain of the JFET type CHEMFET, is also a measure of the chemical properties of the solution under test. By selectively choosing the types of materials which comprise the gate structure, a high degree of chemical selectivity may be achieved. Moreover, by adding a chemically sensitive membrane, even a higher degree of selectivity can be achieved.

The JFET type chemically sensitive transducer disclosed herein is encapsulated so that only the gate structure is exposed to the solution or substance under test. Thus, the entire device may be immersed in the substance or solution, and chemical properties of that substance or solution may be measured by merely noting the variation that occurs in the conductance of the source to drain channel.

Several transducers may also be included on a single substrate chip, each having a different gate structure, and thus each being able to sense a different chemical property.

Finally, the transducers are small enough to facilitate in vivo measurements by inserting the transducers in the lumen of a hollow needle or catheter, thereby allowing the transducers to become part of a real-time in vivo measurement system.

BRIEF DESCRIPTION OF THE DRAWINGS

The above and other objects, features, and advantages of the present invention will become apparent from a consideration of the following detailed description presented in connection with the accompanying drawings, in which.

DESCRIPTION OF THE PREFERRED EMBODIMENTS

A brief description of the operation of a standard JFET device will first be given to help lay the groundwork for the description of the present invention.

Figure 1A:
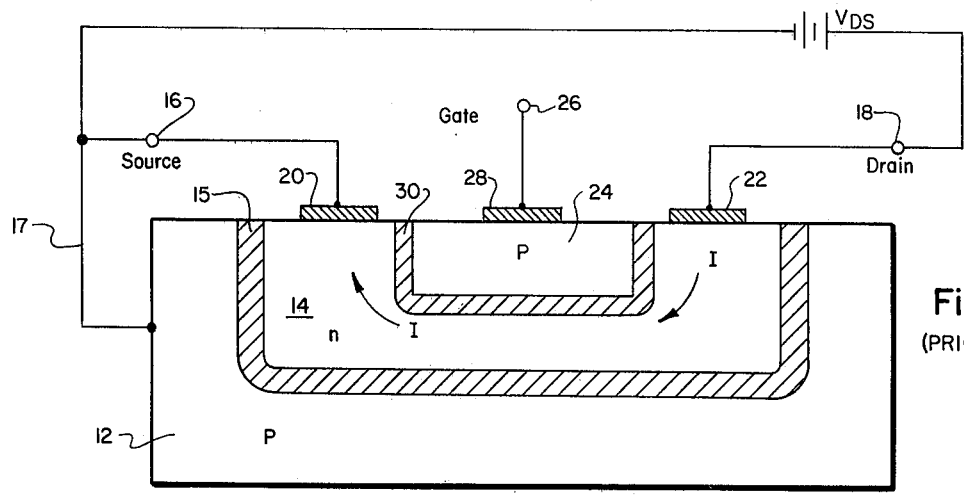
FIGS. 1A, 1B, and 1C symbolically illustrate the principles of operation of a standard JFET device.

FIG. 1A depicts a cross sectional view of a JFET device including a semiconductor substrate 12. This substrate 12 is typically silicon having a p-type doping polarity. At the upper surface of the substrate 12 lies a conducting channel 14, also typically silicon having an n-type doping polarity. At each end of the channel 14 wire terminals 16 and 18 are attached through suitable wire bonding pads 20 and 22 to the channel 14. These terminals 16 and 18 are termed the "Source" and "Drain" respectively. At the interface of the p-doped region 12 and the n-doped region 14, a narrow neutral region 15 is created which is void of all charge carriers.

Overlying the channel 14, between the source 16 and the drain 18, is a gate structure 24. This gate structure 24 is typically comprised of a semiconductor material with a doping polarity opposite to that of the channel 14. Hence, in the embodiment shown in FIG. 1A, the gate structure 24 would typically be silicon having a p-type doping polarity. Another neutral region 30, usually referred to as a depletion region, exists at the interface of the n-doped region 14 with the p-doped gate structure 24. Associated with the gate structure 24 is a wire terminal 26 electrically attached thereto by a bonding pad 28. This terminal 26 is referred to as the "Gate" in standard JFET terminology. When the gate 26 is left disconnected from any external bias potential, as shown in FIG. 1A, then current, represented by the arrows labeled I in FIG. 1A (hereinafter referred to as the current I), may freely flow through the channel 14. The amount of current I that so flows is a function of both the conductivity of the channel 14 (which includes such factors as the semiconductor material, the doping concentration, the geometry of the channel, the temperature, etc.) and the value of an external bias potential, $V_{DS}$, connected between the source and the drain. The substrate 12 is also referenced to the bias potential $V_{DS}$ by an appropriate method, shown symbolically in FIG. 1A as a wire 17 connected to the negative side of $V_{DS}$.

Figure 1B:
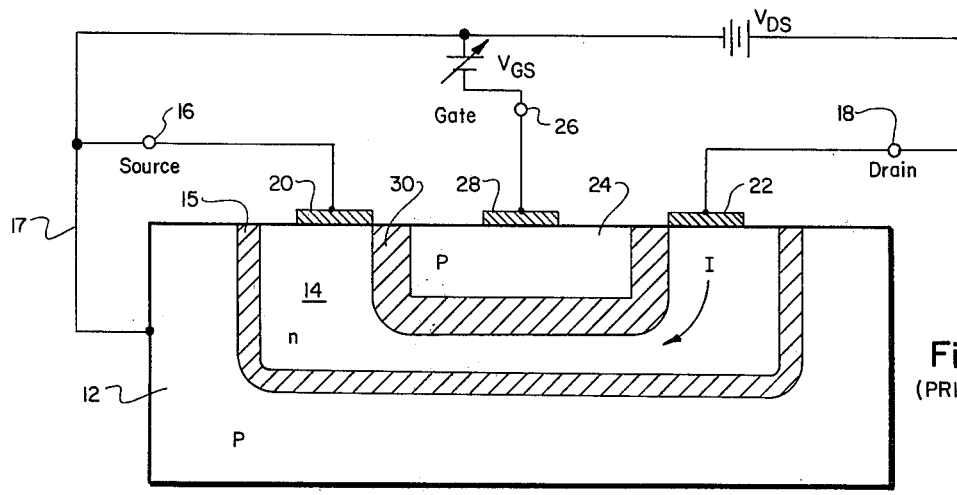

In FIG. 1B, an external bias potential $V_{GS}$, is connected between the gate 26 and the source 16. The polarity of this potential $V_{GS}$ is such that the p-n junction formed by then-channel 14 and the p-gate structure 24 is reverse biased. The effect of such a reverse bias is to attract the positively charged carriers (holes) that exist in the p-doped semiconductor gate structure 24 away from the junction with the n-channel 14. Simultaneously, the electrons in the channel 14 are attracted away from p-doped semiconductor gate structure 24. In this way the region about the boundary between the p-region 24 and the n-region 14 is depleted of charge carriers. This region of depletion, known as the depletion region 30, is void of all free charge carriers, and hence current will not flow therethrough. The effect of the depletion region 30 is to make the n-doped channel 14 narrower, thus decreasing its conductance. Hence, less current I, can flow through the narrower channel 14 of FIG. 1B than could flow through the wider channel 14 of FIG. 1A, even though the same potential $V_{DS}$ is applied between the source and drain of both. In other words, the magnitude of the gate potential $v_{GS}$, as its name implies, acts as a gate, controlling the amount of current I that is allowed to pass through the channel 14.

Figure 1C:
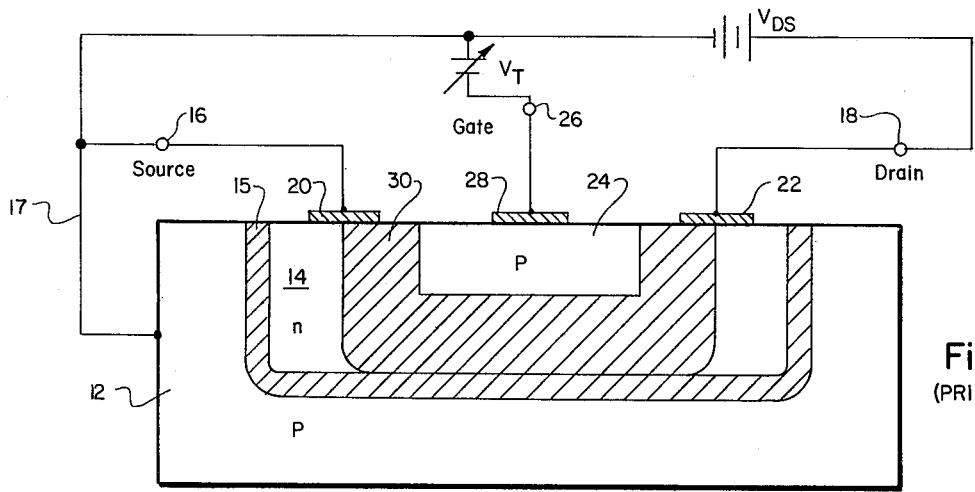

In FIG. 1C, the value of $V_{GS}$ has been increased sufficiently so that the depletion region 30 has reduced the thickness of the channel 14 to zero. The value of $V_{GS}$ required to just close off the channel 14 in this way is appropriately termed the threshold voltage, and is represented in FIG. 1C as $V_T$. With the channel 14 completely depleted in this fashion, no controllable current I can flow through the channel. The only current that flows between the source 20 and the drain 27 is a small leakage current. The amount of such leakage current, however, is no longer controllable by the gate voltage, $V_{GS}$.

While the JFET shown in FIGS. 1A through 1C is an n-channel JFET, built on a p-doped substrate and employing a p-doped gate structure, it is also common in the art to use a p-channel JFET, with an n-doped substrate and n-doped gate structure.

Figure 2:
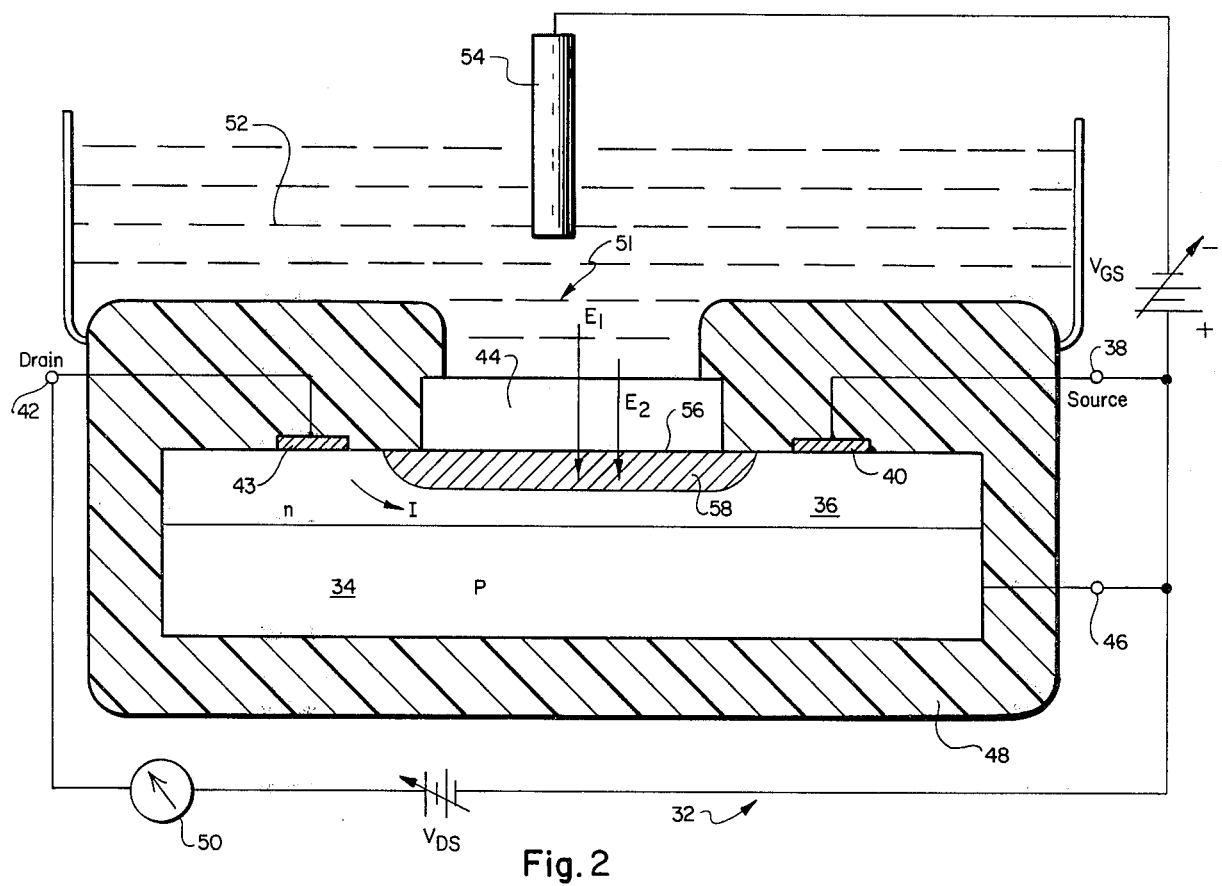
FIG. 2 shows a cross-sectional view of a chemically sensitive FET transducer made in accordance with the present invention wherein the surface structure over the gate region, or the blocking interface, is depicted in a generalized fashion.

Referring now to FIG. 2, there is shown generally a chemically sensitive n-channel JFET transducer 32 of the type disclosed in the present invention. While the n-channel embodiment is the one shown, it is to be understood that the present disclosure also includes a chemically sensitive p-channel JFET. As shown in FIG 2, the chemically sensitive n-channel JFET 32 includes a p-doped semiconductor substrate 34 overwhich an n-doped semiconductor layer 36 is produced. This semiconductor layer 36 provides a channel through which current may flow. A source terminal 38 is electrically connected through a suitable wire bonding pad 40 to one end of the semiconductor 36. Similarly, a drain terminal 42 is electrically connected through a suitable wire bonding pad 43 to the other end of the semiconductor layer 36. A gate structure 44, depicted generally in FIG. 2 as a block or box, lies over the semiconductor layer 36 between the source 38 and the drain 42 so that any current I that flows through the semiconductor layer 36 must flow under the gate structure 44. A terminal 46 is also provided that is electrically connected to the substrate 34. The entire device 32 is encapsuled in a substance impervious encapsulment material 48, such as an epoxy resin, that insulates and protects it from any substance to which it may be exposed. An opening 51 is provided in the encapsulment material 48 to expose the gate structure 44 to whatever substance is being tested. Furthermore, smaller openings allow conductive material, such as wires, to pass through the encapsulment material 48 so that the source terminal 38, drain terminal 42, and substrate terminal 46 may be electrically connected to their respective locations within the device. These smaller openings are appropriately sealed around the wires (or other conductive material) so that only electrical contact can be made with the device therethrough.

The chemically sensitive JFET transducer 32 is operated by connecting an external bias potential $V_{DS}$ between the source terminal 38 and the drain terminal 42. The substrate 34 is also referenced to $V_{DS}$ through the substrate terminal 46. An ammeter 50, or other current measuring device, is connected in series with $V_{DS}$ so that the amount of current I that flows through the channel of the semiconductor layer 36 may be measured. The JFET transducer 32 is then exposed to the solution or substance 52 whose chemical properties are to be measured. Any number of methods may be used to facilitate this exposure. Ideally, the JFET transducer 32 is mounted in the lumen of a needle, catheter, or tube, thus facilitating in vivo measurements in a manner as disclosed with respect to the MOSFET type transducer descibed in U.S. Pat. No. 4,020,830, FIGS. 5A through 7, and text related thereto, which disclosure is incorporated herein by reference.

An additional requirement that must be met before the JFET transducer device 32 will operate is to impart to the substance 52 under test the proper bias potential. A silver/silver chloride, calomel, or other suitable reference electrode 54 is used for this purpose. This electrode 54 is immersed in the solution or material 52, and connected in circuit relationship through another external bias potential $V_{GS}$ with the existing bias potential $V_{DS}$. The bias potential thus imparted to the substance 52 via the reference electrode 54 creates an electric field, represented by the arrow labeled $E_1$ in FIG. 2, whose influence is felt at the junction 56 of the gate structure 44 and the semiconductor layer 36.

The gate structure 44 is adapted to interact with the ions, enzymes, antigens, hormones, antibodies, reducible gases, or any of a variety of chemical and biochemical substances that may be present in the solution or material 52, so as to create a second electric field represented by the arrow labeled $E_2$ in FIG. 2, at the interface 56. The strength of this field $E_2$ is a function of the presence, concentration, or activity of the above chemical or biochemical substances. This chemically sensitive electric field $E_2$ combines with the bias field $E_1$ to produce a resultant electric field at the gate-channel interface 56 which creates a depletion region 58 in the semiconductor layer 36. As with the conventional JFET device referred to in FIGS. 1A, 1B, and 1C, the effect of this depletion region 58 is to make the channel within the layer 36 narrower, i.e., to reduce the amount of current that would otherwise flow therethrough. Hence, by measuring the amount of current that flows at a given value of bias potentials $V_{DS}$ and $V_{CS}$, a measure of the chemical activity of the substance 52 under test is also provided.

The sensitivity of the gate structure 44 to a particular ion, enzyme, antigen, or the like, is heavily influenced by the proper choice of materials for the gate structure 44 and the semiconductor layer 36, or by the inclusion of a chemically sensitive membrane within the gate structure, as disclosed below. Hence, by a proper choice of materials, a chemically sensitive JFET transducer 32 can be fabricated that is sensitive only to a desired chemical or biochemical substance.

An important element of the invention herein disclosed is the blocking interface characteristic of the gate structure 44 when placed over the semiconductor layer 36. As it name implies, this characteristic prevents, or blocks, any significant current from flowing through the gate-channel interface 56. This is an important characteristic because if the current I flowing through the layer 36 is to provide an accurate measure of the chemical or biochemical activity of the solution or material 52 under test (that is, an accurate measure of the electric field strength of $E_2$), then variations in I must be solely attributable to variations in the width of the depletion region 58, and not to variations caused by loss or gain of current through the gate structure 44. This is why prior art chemically sensitive FET devices relied on an insulating material to prevent such current losses or gains (chemically sensitive MOSFETs or IGFETs). However, as the disclosure herein presented makes clear, a proper choice of materials and bias at the gate-channel interface 56 creates the "blocking interface" action that maintains the integrety of the current flow, and thus allows the present invention to use the simpler JFET type device for accurate chemical or biochemical measurements.

The present invention contemplates several embodiments of the gate structure 44. In a first embodiment, shown in FIG. 3, a metal-semiconductor interface, commonly called a Schottky barrier in the semiconductor literature, is used to comprise the blocking interface of a chemically sensitive JFET transducer 32. The interface is made by placing a certain type of metal 60 immediately over the semiconductor layer 36. In order to achieve a desired sensitivity to a particular chemical or biochemical property, both the metal 60 and the semiconductor layer 36 must be properly selected. For example, when the metal 60 is gold, and the semiconductor layer 36 is silicon, gallium arsenide, germanium, or cadmium selenide, a blocking interface gate structure 44 is created which is sensitive to any redox (oxidation reduction) that occurs within the substance 52 under test. Similarly, when the metal 60 is platinum, and the semiconductor layer 36 is gallium arsenide, cadmium arsenide, or cadmium selenide, a blocking interface gate structure 44 is likewise created that is sensitive to redox potential. When the metal 60 is silver, however, and the semiconductor layer 36 is gallium arsenide or cadmium selenide, then the blocking interface gate structure 44 is sensitive to both redox and the silver ion concentration. Another possibility is to use platinum silicide for the metal 60 and silicon for the semiconductor 36. The above cited combination of metals and semiconductors are not meant to be limiting, but are merely cited as examples of how the choice of a particular combination may affect the sensitivity of the gate structure 44.

Figure 3:
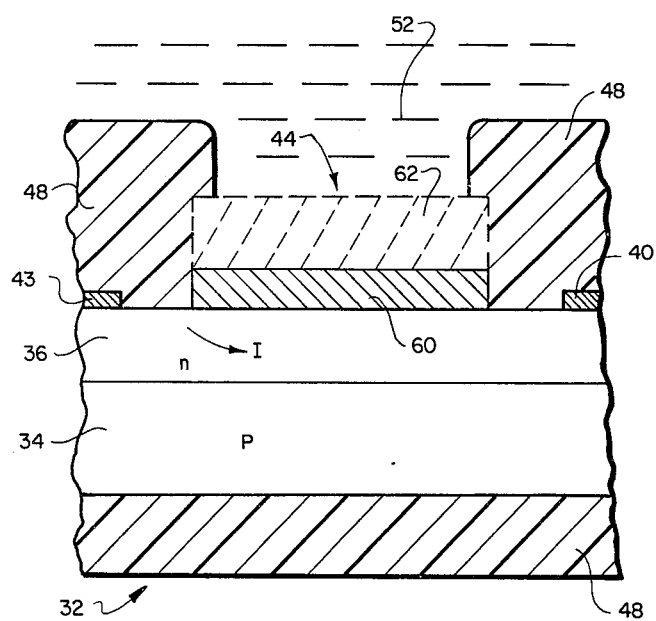
FIG. 3 is a partial cross-sectional view of one embodiment of a chemically sensitive FET transducer as in FIG. 2 wherein the blocking interface is a metal-semiconductor interface, and a chemically sensitive membrane is also employed.

This first embodiment of the gate structure 44 shown in FIG. 3, incorporating the metal-semiconductor blocking interface, may be modified by placing a chemically sensitive membrane system 62 over the top surface of the metal 60. The chemically sensitive membrane system 62 is depicted in FIG. 3 as dotted lines because its use is optional. That is, as discussed above, the transducer 32 will respond to some properties of the substance 52 under test without the use of the membrane system 62. Use of the membrane system 62, however, allows the transducer 32 to be more selective as described below.

The membrane system 62 is ion selective; that is, the membrane system 62 selectively absorbs or interacts with particular chemical ions from the substance 52 under test so as to sensitize or desensitize the chemically sensitive JFET transducer 32 to that particular ion. The chemically sensitive membrane system 62 may be any of the types described in U.S. Pat. No. 4,020,830 for use in conjunction with the chemically sensitive MOSFET or IGFET type transducer, which disclosure is incorporated herein by reference. Typically, the membrane system 62 will be a polyvinyl-chloride-valiomycin-plasticizer, sensitive to potassium ions; or a silver/silver chloride membrane which is sensitive to chloride ions and silver ions.

Figure 4:
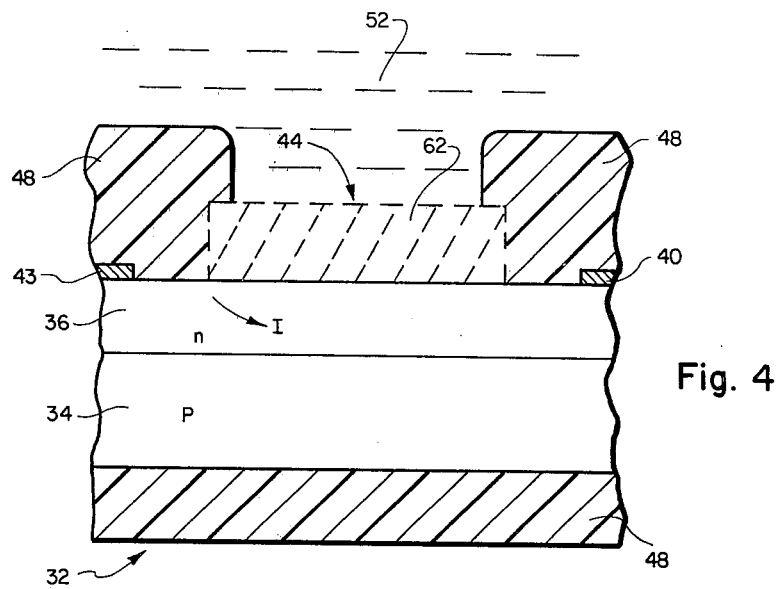
FIG. 4 is a partial cross-sectional view of another embodiment of a chemically sensitive FET transducer made in accordance with the present invention wherein the blocking interface is merely a solution-semiconductor interface, and a chemically sensitive membrane is also employed.

A second embodiment of the blocking interface gate structure 44 is shown in the partial cross sectional view of the chemically sensitive JFET transducer 32 of FIG. 4. This second embodiment incorporates a solution-semiconductor interface, and is commonly referred to as a blocking electrode in the electrochemical literature. As with the metal-semiconductor blocking interface discussed above in connection with FIG. 3, a chemically sensitive membrane system 62 may be added to the solution-semiconductor interface in order to make the overall gate structure 44 more selective to desired chemical or biochemical properties. However, even without the chemically sensitive membrane system 62, the solution-semiconductor interface may be made sensitive to some properties of the substance 52 under test by proper selection of the type of material used in the semiconductor layer 36 and by proper setting of the bias potential $V_{GS}$ (FIG. 2). Exemplary semiconductor materials and their corresponding sensitivities include: (1) cadmium sulfide, sensitive to a concentration of cadmium and sulfide ions; (2) silver sulfide, sensitive to a concentration of silver and sulfide ions; (3) gallium arsenide, sensitive to redox potential; and (4) indium phosphide, also sensitive to redox potential.

Figure 5:
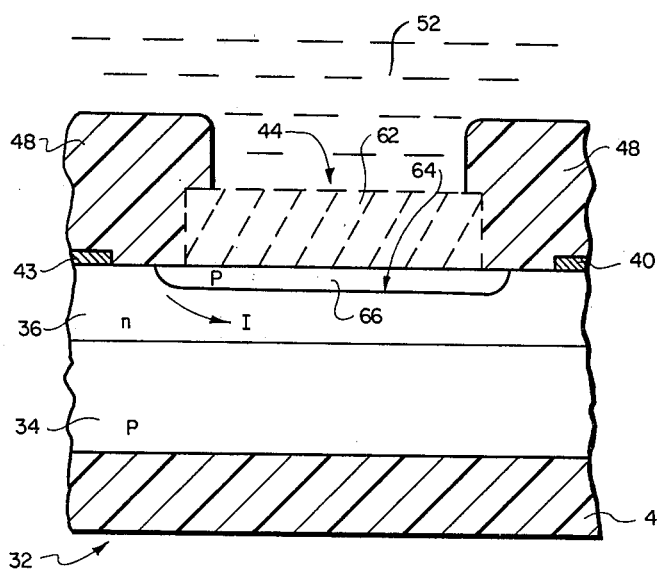
FIG. 5 is a partial cross-sectional view of still another embodiment of a chemically sensitive FET transducer made in accordance with the present invention wherein the blocking interface is a P-N junction, and a chemically sensitive membrane is also employed.

A third embodiment of the blocking interface gate structure 44 is shown in the partial cross sectional view of the chemically sensitive JFET transducer 32 of FIG. 5. This third embodiment incorporates a p-semiconductor to n-semiconductor interface 64, commonly called a p-n junction in the semiconductor literature. As FIG. 5 illustrates, this embodiment includes the same elements as disclosed in FIG. 2, i.e., a substrate 34, a semiconductor layer 36 through which an electrical current may flow, bonding pads 40 and 43 associated with the Source and Drain terminals respectively, and encapsulment material 48 exposing only the gate structure 44 to the substance 52 under test. The gate structure 44 of this third embodiment, however, includes a thin layer of gate semiconductor material 66, having a doping polarity opposite to that of the semiconductor layer 36, and overlying that portion of the layer 36 between the source and drain contacts or pads 40 and 43. Thus, in the embodiment shown in FIG. 5, where the semiconductor layer 36 is n-doped, the gate semiconductorlayer 64 would be p-doped. By properly referencing the bias potentials associated with the p-n junction 64 between the semiconductor layers 66 and 36, the junction 64 may be reverse biased, thus creating the desired blocking interface action. Such biasing is achieved by proper setting of the external bias potentials $V_{GS}$ and $V_{DS}$ (FIG. 2). Moreover, by properly selecting the type of semiconductor materials used on each side of the p-n junction interface 64, the gate structure 44 may be made sensitive to desired chemical properties. For example, if the semiconductor layer 36 is n-doped gallium arsenide, and the gate semiconductor layer 66 is p-doped indium phosphide, then the p-n junction thus formed would be sensitive to all redoxes occurring in the substance 52 under test. The same would be true for any combination of the above materials and doping, e.g., the semiconductor layer 36 could be p-doped indium phosphide, while the gate semiconductor layer could be n-doped gallium arsenide. The semiconductor layer 36 and the gate semiconductor layer 66 may be the same semiconductor material with opposite (p and n) doping, or they may be different semiconductor materials as in the examples above.

As with the previous two embodiments of the gate structure 44, discussed in connection with FIGS. 3 and 4, a chemically sensitive membrane system 62 may be used in conjunction with the p-n junction gate structure of FIG. 5 in order to improve its sensitivity to desired chemical properties. If used, the membrane system 62 would be of the same type discussed supra.

Figure 6:
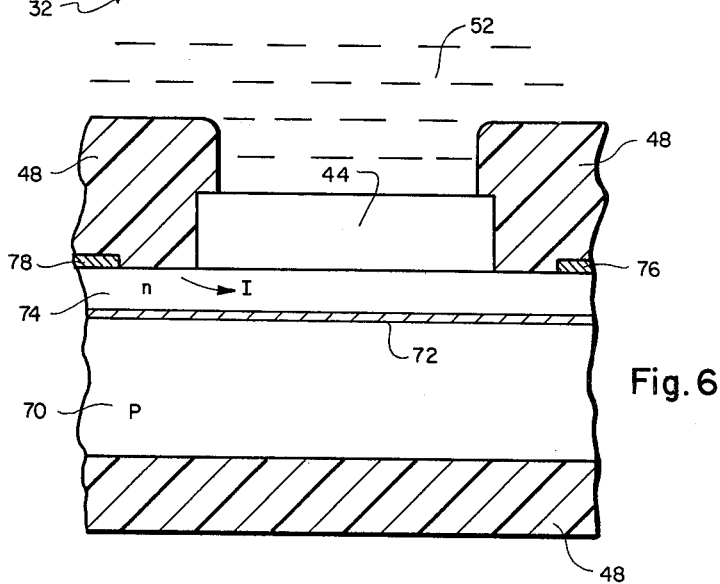
FIG. 6 is a partial cross-sectional view of a chemically sensitive FET transducer made in accordance with the present invention illustrating the use of a thin film of semi-conductor on an insulating substrate as an alternative to the method of construction depicted in FIGS. 1-5.

Referring now to FIG. 6, there is shown a partial cross sectional view of another embodiment of a chemically sensitive JFET transducer made in accordance with the present invention. The embodiment disclosed in FIG. 6 incorporates a substrate material 70 over which an insulating material 72 is laid. On top of the insulating layer 72 a thin semiconductor layer 74 is placed. Source and drain terminals are electrically connected to the ends of this semiconductor layer 74 through bonding pads 76 and 78 respectively, thus allowing an electrical current I to flow from the source to the drain, or vice-versa, whenever a voltage potential is connected therebetween. A gate structure 44, of any of the types disclosed supra, overlies the thin semiconductor layer 74 between the source and drain contacts 76 and 78. Encapsulment material 48 protects all but the gate structure 44 from being exposed to the substance 52 under test. The device can also be made by chosing a suitable substrate 70 which is an electrically insulating material through which an electric current will not flow. Once this is done, there is no need for the thin layer of insulating material 72. Exemplary materials for such an insulating substrate include sapphire or spinel. Even a semi-insulating material, such as semi-insulating gallium arsinide, may be used as the insulating substrate inasmuch as only very small currents may flow therethrough.

The operation of the transducer shown in FIG. 6 is basically the same as that disclosed previously with respect to the transducer shown in FIG. 2. That is, the gate structure 44 interacts with the semiconductor layer 74 in such a way that a depletion region is created in the thin semiconductor layer 74. The chemical activity of the substance 52 interacts with the gate structure 44 and modulates the thickness of this depletion region. This depletion region depletes the current I flowing through the layer 74 as a function of said chemical activity, as discussed previously in connection with the transducer shown in FIG. 2.

There is, however, one important difference between the transducer of FIG. 6 and that of FIG. 2. In FIG. 2, the p-doped substrate 34 is reverse biased or zero biased with respect to the n-doped semiconductor layer 36. This reverse bias (meaning the n-doped semiconductor is positive with respect to the p-doped semiconductor) or zero bias restricts all of the source-drain current to flow in the semiconductor layer 36 and prevents it from flowing in the substrate 34. In FIG. 6, the insulating layer 72 on an insulated substrate 70 provides this same function of restricting the source-drain current to the semiconductor layer 74. Thus, there is no need to reverse bias the substrate 70 of the embodiment disclosed in FIG. 6.

Regardless of the embodiment of the invention that is used, there are a couple of design considerations imposed by the mechanism of the JFET type of device that must not be overlooked. First, the thickness of the semiconductor layer (through which the source-drain current flows) must be only slightly greater than the depletion layer thickness. This means that the semiconductor layer must be lightly doped in order to get as large a depletion layer thickness as possible for the relatively small electric fields that are generated at the gate-channel interface of a CHEMFET device. Typically, depletion layers range from 0.1 to 10 micrometers thick. Thus, the semiconductor layer must be on the order of 1 micrometer thick.

Second, the source-drain current must be restricted to flow under the gate structure only. This is because source-drain current which does not flow under the gate structure is not affected by the properties of the solution, so such current contributes nothing to the sensitivity of the transducer. In fact, such current detracts from the sensitivity of the transducer because the ratio of depleted current to non-depleted current decreases.

Figure 7A:
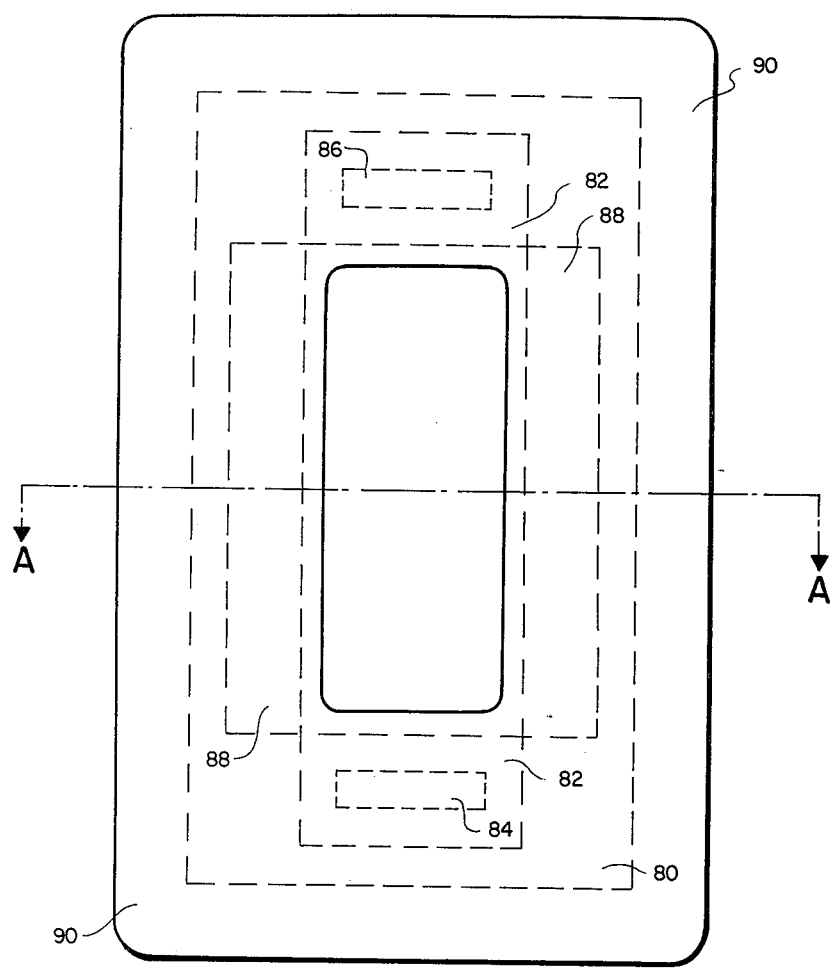
FIG. 7A shows a top view of a chemically sensitive FET transducer made in accordance with the present invention depicting a method of construction that can be used to restrict the source-drain current to flow under the blocking interface.
Figure 7B:
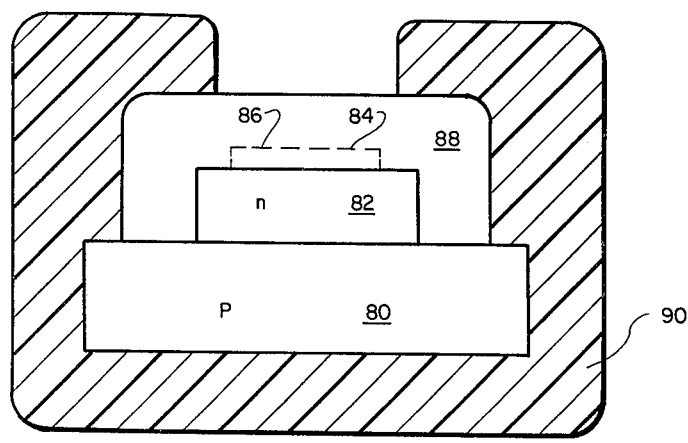
FIG. 7B shows a cross-sectional view taken along the line A—A in FIG. 7A.

Several methods can be used to restrict all the source-drain current to flow under the gate structure. One such method is to use a configuration as shown in FIGS. 7A and 7B. This method comprises etching the semiconductor layer so that it is removed outside the area covered by the gate structure. FIG. 7A is a top view of a chemically sensitive JFET transducer in which this has been done. FIG. 7B is a cross sectional view of the same device taken along the line A—A in FIG. 7A.

Referring to FIGS. 7A and 7B there is shown a substrate material 80 over which a semiconductor layer 82 is laid. Source and drain contact pads, 84 and 86 respectively, are attached to opposite ends of the semiconductor layer 82 so that current may be forced to flow therethrough. A chemically sensitive blocking interface gate structure 88 overlies the top and sides of the semiconductor layer 82. Encapsulment material 90 completely surrounds the entire transducer, allowing only the gate structure 88 to be exposed to the substance under test. As can be seen from the configuration of FIGS. 7A and 7B, substantially all of the source-drain current must pass underneath the gate structure, as desired.

Figure 8A:
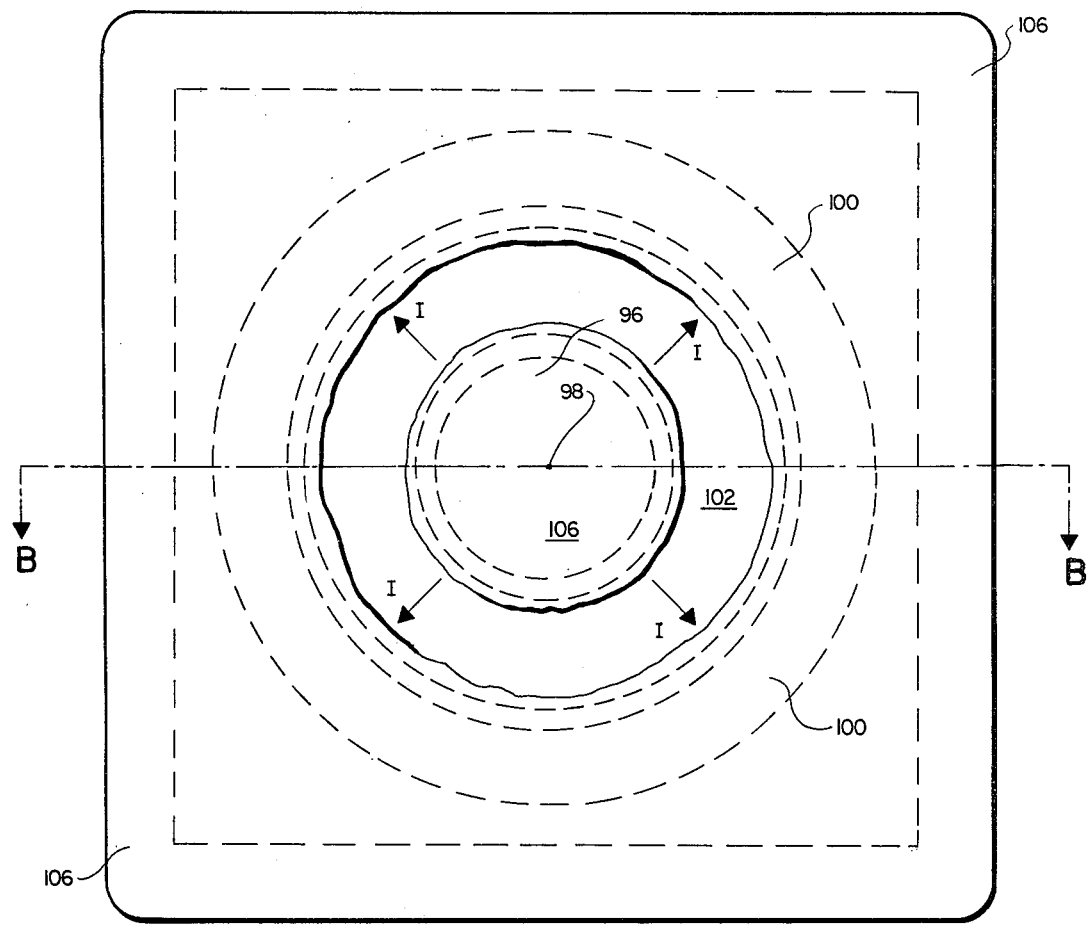
FIG. 8A and 8B likewise show cross-sectional tipe and cross-sectional side views respectively of an alternative method of construction that can be used in connection with the present invention to restrict the flow of source-drain current to the area underneath the blocking interface, the cross-section of FIG. 8B being taken along the line B—B in FIG. 8A.
Figure 8B:
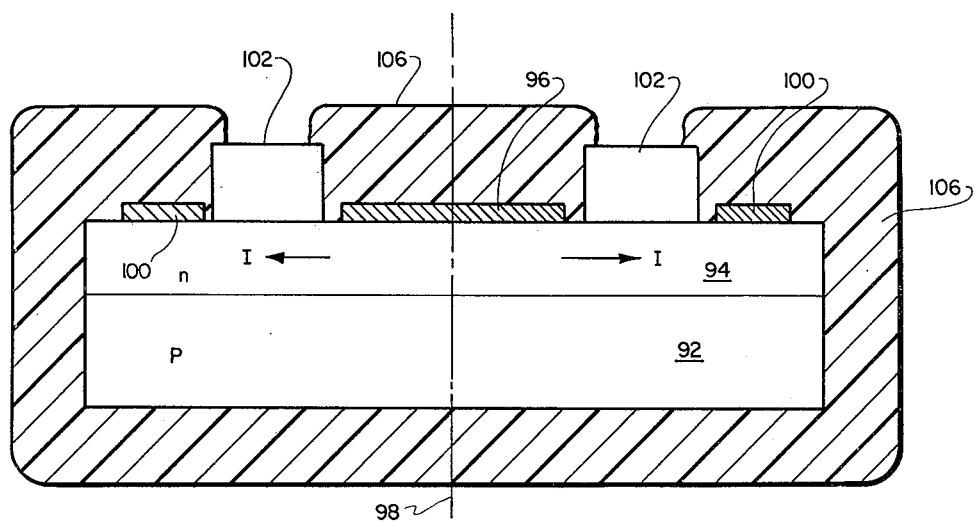

A second method of forcing all the source-drain current to flow under the gate structure is to use a "closed" configuration as shown in FIGS. 8A and 8B. FIG. 8A is a top view of a transducer employing such a closed configuration, and FIG. 8B is a cross sectional side view of the same device taken along the line B—B in FIG. 8A. The configuration employs a substrate material 92 over which is laid a semiconductive layer 94. A source contact 96 makes electrical contact with the semiconductor layer 94 at the center thereof being symetrically positioned around a center axis 98. Also symetrically placed around the center axis 98, but at a spaced distance therefrom, is a closed source contact 100. In FIGS. 8A and 8B this source contact 100 is circular or ring shaped, although any similar closed geometrical shape would suffice. Source-drain current I thus flows radially from the centrally located source contact 96 to the ring shaped drain contact 100, or vice-versa.

Still referring to FIGS. 8A and 8B, a closed geometrically shaped blocking interface gate structure 102, symetrically positioned from the center axis 98, overlies that portion of the semiconductor layer 94 that lies between the source contact 96 and the ring shaped drain contact 100. Thus, all of the source-drain current I that flows radially between the source and drain contacts 96 and 100 respectively is forced to pass under the gate structure 102. As with all the other embodiments of the invention herein disclosed, encapsulment material 106 may be used to protect the transducer device from the substance under test, allowing only the gate structure 102 to be exposed thereto.

Figure 9:
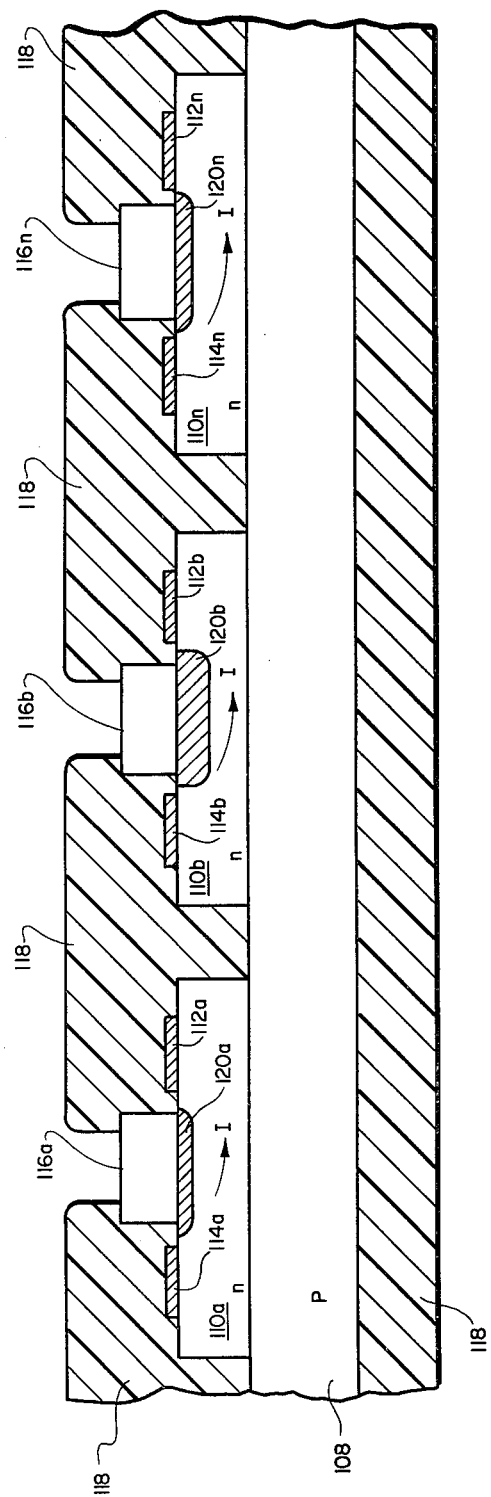
FIG. 9 is a partial cross-sectional view of still another embodiment of the invention that implements a plurality of chemical sensitive JFET transducers fabricated on a single substrate material.

Referring now to FIG. 9 there is shown a partial cross sectional view of still another embodiment of the present invention that incorporates a plurality of chemically sensitive JFET transducers on the same substrate material. A substrate material 108, shown as p-doped in FIG. 9, has a plurality of independent semiconductor layers 110a, 110b, -110n, of opposite doping polarity, placed on the upper surface thereof. Associated with each semiconductor layer 110a, 110b, -110n, is a source contact 112a, 112b, -112n, a drain contact 114a, 114b, -114n, and a chemically sensitive blocking interface gate structure 116a, 116b, -116n. Each of these gate structures 116a, 116b, -116n may be any of the types disclosed previously in connection with the discussion of FIG. 3, 4 and 5. Usually, each of these gate structures would respond to a different property of the solution; thus each subdevice a, b, -, n would respond to a different property of the solution. Moreover, while the method depicted in FIG. 9 for restricting the source-drain current to flow under the gate structure comports with that disclosed in FIGS. 7A and 7B, the method disclosed in FIGS. 8A and 8B could also be used. Likewise, the method of restricting the current from flowing in the substrate 108 could be either of the previously discussed methods (reverse biased p-n junction or insulting substrate).

Also used with the multi-sensor transducer of FIG. 9 is encapsulment material 118 to protect all but the gate structures 116a, 116b, -116n from exposure to the substance under test. As each of these gate structures independently interacts with the substance under test, a depletion region 120a, 120b, -120n is created in the semiconductor layer 110a, 110b, -110n in accordance with the principles and manner described previously in connection with FIG. 2. This depletion region affects the conductivity of the semiconductor layer to such a degree that a measure of the current allowed to flow therethrough represents an accurate measure of the chemical or biochemical activity of the substance under test.

Effective use of a chemically sensitive JFET transducer of the type herein disclosed depends on accurate calibration thereof, as well as the use of stable instrumentation equipment and the implementation of the design considerations previously discussed. In reference to FIG. 2, for example, the external bias potentials $V_{DS}$ and $V_{GS}$ must be stable with little or no drift inasmuch as both of these bias potentials directly influence the amount of source-drain current I that will flow through the semiconductor layer 36. Similarly, the reference electrode 54 must make good electrical contact with the substance 52 under test so as to impart a stable bias potential thereto which will be transferred to the blocking interface gate structure 44 so as to allow it to perform its proper functions. Furthermore, the ammeter 50, or other instrumentation equipment used to measure the level of the source-drain current, must be sufficiently sensitive to the minor changes in the source-drain current I that signal a change in chemical activity.

Calibration of the chemically sensitive JFET transducer comprises exposing the transducer to a controlled substance, i.e., one with known chemical and physical properties at known quantitative levels, while maintaining stable bias potentials as above mentioned, and measuring and recording the level of source-drain current I which flows through the device. The transducer is thus exposed to a controlled substance having the same known physical and chemical properties, but at a slightly different quantitative level, and the change in source-drain current I is noted. By repeating this process again and again, accurate calibration data can be obtained that indicates what value of source-drain current corresponds to a known chemical or biochemical activity of the substance under test for the type of transducer that is used at the given bias levels and physical conditions.

As shown and described in the above paragraphs, and corresponding Figures, an inexpensive, simple to construct, and yet rugged chemically sensitive JFET transducer may be created. The transducer provides the capibility for measuring on-site signals that are produced in response to detected chemical properties. The arrangement is compact and versatile and may be easily adapted for use with a variety of insertion devices and measurement methods.

It is to be understood that the above-described arrangements are only illustrative of the application of the principles of the present invention. Numerous other modifications and alternative arrangements may be devised by those skilled in the art without departing from the spirit and scope of the present invention and the appended claims are intended to cover such modifications and arrangements.

What is claimed is:

1. A chemical sensitive junction field-effect transistor transducer for detecting chemical properties of substances to which said transducer is exposed comprising:
   (a) a substrate material;
   (b) a semiconductor layer having a doping polarity located at an upper surface of said substrate material, said doping polarity enabling an electrical current to flow through said layer;
   (c) means for electrically connecting spaced apart regions of said semiconductor layer to an external voltage source, thereby allowing an electrical current to flow from said voltage source to a first of said spaced apart regions through a first of said electrical connecting means, through said semiconductor layer to a second of said spaced apart regions, and from said second spaced apart region through a second of said electrical connecting means back to said external voltage source;
   (d) a blocking interface overlying that portion of said semiconductor layer that lies between said spaced apart regions and through which said electrical current flows, said blocking interface being adapted to interact with said substance so as to generate an electrical potential at said interface whose strength is a measure of selected chemical properties of said substance, said blocking interface having no insulating layer as a part thereof;

(e) a reference electrode connected in circuit relationship with said semiconductor layer through a second external voltage source such that a potential is created and added to the electric potential generated at said blocking interface, thus creating a resultant electric field that affects the conductivity of said semiconductor layer as a measure of the chemical properties of said substances by modulating the thickness of a depletion layer in the upper surface of said semiconductor layer which is void of free charge carriers, said depletion layer having a thickness related to said resultant electric field.

2. A transducer as defined in claim 1 wherein said blocking interface comprises a metal-semiconductor blocking interface comprising a conductive metal in combination with said semiconductor layer, said conductive metal being selectively chosen to react with desired ions, enzymes, antibodies, antigens, and the like so as to generate an electrical potential within said gate structure that varies as a measure of the presence, concentration, and activity of said ions, enzymes, antibodies, antigens, and the like within the substance to which said transducer is exposed.

3. A transducer as defined in claim 2 wherein said conductive metal is gold and said semiconductor layer is selected from a group of semiconductor materials consisting of silicon, gallium arsenide, germanium, and cadmium selenide.

4. A transducer as defined in claim 2 wherein said conductive metal is platinum and said semiconductor is selected from a group consisting of gallium arsenide, cadmium selenide, and cadmium sulfide.

5. A transducer as defined in claim 2 wherein said conductive metal is silver and said semiconductor is selected from a group consisting of gallium arsenide and cadmium sulfide.

6. A transducer as defined in claim 2 wherein said conductive metal is platinum silicide and said semiconductor is silicon.

7. A transducer as defined in claim 2 further comprising a chemical selective membrane overlying said conductive metal, said membrane adapted to selectively interact with ions, enzymes, antibodies, antigens, and the like, so as to change the electrical potential at the surface of said membrane, said potential change thereby contributing to the resultant electric field that affects the conductivity of said semiconductor layer.

8. A transducer as defined in claim 7 wherein said chemical selective membrane is selected from the group consisting of polyvinylchloride-valiomycin-plasticer and silver/silver choride.

9. A transducer as defined in claim 1 wherein said blocking interface comprises a solution-semiconductor blocking interface comprising the combination of said semiconductor layer being selectively chosen to react with desired ions, enzymes, antibodies, antigens, and the like so as to generate a potential at said gate structure that varies as a measure of the presence, concentration, and activity of said ions, enzymes, antibodies, antigens, and the like within said substance.

10. A transducer as defined in claim 9 wherein said semiconductor layer is selected from a group of semiconductor materials consisting of cadmium sulfide, silver sulfide, gallium arsenide, and indium phosphide.

11. A transducer as defined in claim 9 further comprising a chemical selective membrane overlying said semiconductor layer, said membrane adapted to selectively react with ions, enzymes, antibodies, antigens, and the like, so as to change the electrical potential at the surface of said membrane, said potential change thereby contributing to the resultant electric field that affects the conductivity of said semiconductor layer.

12. A transducer as defined in claim 1 wherein said blocking interface comprises a reverse biased p-n junction blocking interface comprising a p-doped semiconductor interfaced with an n-doped semiconductor, said semiconductor types being selectively chosen so as to be sensitive to specific chemical properties of said substance.

13. A transducer as defined in claim 12 wherein said p-doped semiconductor and n-doped semiconductor are selected from a group of semiconductor materials consisting of silicon, germanium, gallium arsenide, and indium phosphide.

14. A transducer as defined in claim 12 further comprising a chemical selective membrane adapted to selectively react with ions, enzymes, antibodies, antigens, and the like, so as to change the electrical potential at the surface of said chemical selective membrane, said potential change thereby contributing to the resultant electric field that affects the conductivity of said semiconductor layer.

15. A transducer as defined in claim 1 wherein said semiconductor layer is only slightly thicker than said depletion layer.

16. A transducer as defined in claim 15 wherein said semiconductor layer is on the order of one micrometer thick, being at least 0.1 micrometer thick and not greater than 10 micrometers thick.

17. A transducer as defined in claim 1 further including means for channeling the electrical current that passes through said semiconductor layer to flow under said blocking interface.

18. A transducer as defined in claim 17 wherein said channeling means comprises a physical configuration wherein said semiconductor layer only exists immediately underneath said blocking interface.

19. A transducer as defined in claim 18 wherein said physical configuration comprises a rectangular shaped strip of semiconductor layer immediately underneath a rectangular-shaped blocking interface of approximately the same dimensions, said means for electrically connecting the spaced apart regions of said semiconductor layer being attached to opposite ends of said rectangular semiconductor layer strip.

20. A transducer as defined in claim 18 wherein said physical configuration comprises a semiconductor layer of a closed geometrical shape to which said first electrical connecting means is attached at the center thereof and said second electrical connecting means is attached around the perimeter thereof, thereby allowing electrical current to flow in a radial pattern between said center and perimeter, such as a circular shaped semiconductor layer with electrical connecting means attached at the center and circumference thereof so as to allow electrical current to flow in a radial pattern between the center and the circumference, and further including similar closed geometrically shaped gate structure placed over those regions of said closed geometrically shaped semiconductor layer through which the radial electrical currents flow.

21. A transducer as defined in claim 1 wherein said substrate material comprises a semiconductor substrate material and further comprising means for preventing the electrical current flowing through said semiconductor layer from flowing in said semiconductor substrate.

22. A transducer as defined in claim 21 wherein the semiconductor substrate material has a doping polarity opposite that of said semiconductor layer and further wherein said prevention means comprises reverse biasing the semiconductor junction formed by said semiconductor substrate and semiconductor layer.

23. A transducer as defined in claim 21 wherein said prevention means comprises an insulator that electrically insulates said substrate from said semiconductor layer.

24. A transducer as defined in claim 1 wherein said substrate material comprises an electrically insulating material that precludes significant electric currents from flowing therein.

25. A transducer as defined in claim 24 wherein said semiconductor layer is silicon and said insulating substrate is chosen from the group consisting of spinel and sapphire.

26. A transducer as defined in claim 24 wherein said semiconductor layer is gallium arsenide and said insulating substrate is semi-insulating gallium arsenide.

27. A transducer as defined in claim 1 further comprising a substance impervious material disposed over said substrate material, semiconductor layer, and gate structure, with an opening therein for exposing a portion of said gate structure to the substances to which said transducer is exposed.

28. A multi-sensor chemically sensitive junction field effect transistor (JFET) for detecting chemical properties of substances to which said transducer is exposed comprising
 (a) a substrate material;
 (b) a plurality of independent semiconductor layers having a doping polarity located at an upper surface of said substrate material;
 (c) means for electrically connecting spaced apart regions of each of said independent semiconductor layers to an external voltage source, thereby allowing electrical current to flow to, through, and from each of said semiconductor layers;
 (d) a plurality of chemical sensitive blocking interfaces, one of which overlies that portion of each of said plurality of semiconductor layers that lies between said spaced apart regions and through which said electrical current flows, each of said blocking interfaces being adapted to interact with said substances so as to generate an electric potential at said interfaces whose strength is a measure of selected chemical properties of said substances, each of said blocking interfaces having no insulating layer as a part thereof;
 (e) a reference electrode connected in circuit relationship with each of said semiconductor layers through a second external voltage source such that a potential is created and added to the electric potential generated at each of said blocking interfaces, a resultant electric field that affects the conductivity of each of said semiconductor layers as a measure of the chemical properties of said substances by inducing a depletion layer in the upper surface of each of said semiconductor layers which is void of free charge carriers, said depletion layer having a thickness proportional to said resultant electric field.

29. A multi-sensor transducer as defined in claim 28 wherein at least one of said plurality of blocking interfaces comprises a metal-semiconductor blocking interface comprising a conductive metal, in combination with said semiconductor layer.

30. A multisensor transducer as defined in claim 29 wherein the semiconductor layer associated with said metal-semiconductor blocking interface is selected from the group consisting of silicon, gallium arsenide, germanium, and cadmium selenide.

31. A multi-sensor transducer as defined in claim 28 wherein at least one of said plurality of blocking interfaces comprises a solution-semiconductor blocking interface comprising the combination of said semiconductor layer and said substance to which the transducer is exposed.

32. A multi-sensor transducer as defined in claim 31 wherein the semiconductor layer associated with said solution-semiconductor blocking interface is selected from the group consisting of cadmium sulfide, silver sulfide, gallium arsenide, and indium phosphide.

33. A multi-sensor transducer as defined in claim 28 wherein at least one of said plurality of blocking interfaces comprises a reverse biased p-n junction blocking interface, comprising a p-doped semiconductor interfaced with an n-doped semiconductor.

34. A multi-sensor transducer as defined in claim 33 wherein said p-doped semiconductor and n-doped semiconductor are selected from the group consisting of gallium arsenide and indium phosphide.

35. A multi-sensor transducer as defined in claim 28 further including at least one chemical selective membrane overlying one of said blocking interfaces, said chemical selective membrane adapted to selectively interact with ions, enzymes, antibodies, antigens, and the like, found in the substance to which said multi-sensor transducer is exposed so as to change the electrical potential at the surface of said chemical selective membrane, said potential change thereby contributing to the resultant electric field that affects the conductivity of the semiconductor layer over which said chemical selective membrane is laid.

36. A multi-sensor transducer as defined in claim 28 further including a substance impervious material disposed over said substrate material, semiconductor layers, and blocking interfaces, with a plurality of openings therein for exposing a portion of each of said gate structures to said substances to which said multi-sensor transducer is exposed.

37. A method of configuring a chemical sensitive junction field effect transistor (JFET) transducer comprising a substrate, a doped semiconductor layer on the surface of said substrate, conductive material electrically connected to a pair of spaced apart areas on said semiconductor layer, one of said areas being designated the drain and the other being designated the source, a blocking interface overlying that portion of said semiconductor layer lying between said spaced apart means, and a reference electrode connected in circuit relationship with said semiconductor layer, said chemical sensitive JFET configuration method being adapted to force electrical current flowing between the source and drain to flow under said blocking interface, said method comprising the steps of:
 (a) configuring a shaped semiconductor layer, such as a circle, on the upper surface of said substrate;
 (b) connecting a conductive material, such as a wire, to the center of said shaped semiconductor layer, said center serving as the source of said transducer;
 (c) connecting other conductive material around the perimeter of said shaped semiconductor layer, said perimeter serving as the drain of said transducer; and
 (d) configuring said blocking interface in a symmetrical fashion above the area of said semiconductor layer that lies between said source and drain.

* * * * *